(12) United States Patent
Pinchuk

(10) Patent No.: US 9,649,223 B2
(45) Date of Patent: May 16, 2017

(54) INSERTER FOR TUBULAR MEDICAL IMPLANT DEVICES

(71) Applicant: InnFocus, Inc., Miami, FL (US)

(72) Inventor: Leonard Pinchuk, Miami, FL (US)

(73) Assignee: INNFOCUS, INC., Miami, FL (US)

(*) Notice: Subject to any disclaimer, the term of this patent is extended or adjusted under 35 U.S.C. 154(b) by 164 days.

(21) Appl. No.: 14/299,622

(22) Filed: Jun. 9, 2014

(65) Prior Publication Data
US 2014/0371651 A1 Dec. 18, 2014

Related U.S. Application Data

(60) Provisional application No. 61/834,609, filed on Jun. 13, 2013.

(51) Int. Cl.
*A61F 11/00* (2006.01)
*A61F 9/007* (2006.01)

(52) U.S. Cl.
CPC .................. *A61F 9/00781* (2013.01)

(58) Field of Classification Search
CPC .......... A61F 9/00781; A61F 2/46; A61F 2/14; A61M 27/002; A61B 2017/0409
USPC .............................. 606/108, 232, 139; 604/8
See application file for complete search history.

(56) References Cited

U.S. PATENT DOCUMENTS

| | | | |
|---|---|---|---|
| 5,591,184 A * | 1/1997 | McDonnell | A61B 17/3203 604/22 |
| 5,735,858 A | 4/1998 | Makker et al. | |
| 7,186,232 B1 | 3/2007 | Smedley et al. | |
| 7,431,709 B2 | 10/2008 | Pinchuk et al. | |
| 7,837,644 B2 | 11/2010 | Pinchuk et al. | |
| 2002/0133168 A1* | 9/2002 | Smedley | A61F 9/00781 606/108 |
| 2004/0236343 A1 | 11/2004 | Taylor et al. | |
| 2005/0154399 A1 | 7/2005 | Weber et al. | |
| 2007/0276316 A1 | 11/2007 | Haffner et al. | |
| 2008/0228127 A1* | 9/2008 | Burns | A61F 9/00781 604/9 |
| 2010/0222802 A1* | 9/2010 | Gillespie, Jr. | A61M 25/10 606/192 |
| 2013/0144334 A1* | 6/2013 | Bouduban | A61B 17/0401 606/232 |
| 2014/0114330 A1* | 4/2014 | Karasic | A61B 17/0401 606/144 |
| 2014/0257383 A1* | 9/2014 | Lombardo | A61B 17/0401 606/232 |

* cited by examiner

*Primary Examiner* — Melanie Tyson
*Assistant Examiner* — Erich Herbermann
(74) *Attorney, Agent, or Firm* — Gordon & Jacobson, P.C.

(57) ABSTRACT

An inserter is provided for inserting a tubular medical implant device into tissue. The inserter includes a rigid rod extending along a longitudinal axis. The rod has a distal portion that defines an open slot. The open slot extends diametrically through the rod along the longitudinal axis to a base. The open slot is configured to receive and release the tubular medical implant device.

31 Claims, 5 Drawing Sheets

INSERTER FOR TUBULAR MEDICAL IMPLANT DEVICES

CROSS-REFERENCE TO RELATED APPLICATIONS

This application claims priority to provisional application 61/834,609, filed Jun. 13, 2013, the entire contents of which are incorporated herein by reference.

BACKGROUND

1. Field

The present application relates to medical device implants. More particularly, the present application relates to devices for inserting a tubular medical device implant into the body (specifically, into the eye).

2. State of the Art

Glaucoma is a buildup of pressure in the eye which can impinge on the blood supply feeding the optic nerve. Such buildup of pressure in the eye, if left unchecked, can damage the optic nerve, resulting in vision loss and blindness. Various shunts and tools for shunts have been proposed for relieving the buildup of pressure.

U.S. Pat. No. 7,431,709 describes a glaucoma drainage shunt made from a soft material, e.g., SIBS. FIG. 1 shows the glaucoma drainage shunt 1 of U.S. Pat. No. 7,431,709, which includes a small tube 2 with a tab 3 located approximately halfway down the length of the tube. The lumen of the tube 2 is 50 to 100 μm in diameter. The tab 3 prevents migration of tube 2 into the eye, which can occur while blinking; that is, the eyelid pushes the tube into the eye.

The glaucoma drainage shunt 1 of FIGS. 1 and 2 minimizes the buildup of pressure in the eye for treatment of glaucoma. The glaucoma drainage shunt 1 is delivered into the eye such that the entrance to the tube the distal end (D) is in the anterior chamber of the eye and the proximal end (P), or drainage end of the glaucoma drainage shunt 1 is in a pocket or space between the conjunctiva/tenons and sclera wherein the space fills with drained aqueous humor and forms a blister-like reservoir called a bleb (FIG. 2). Aqueous humor can accumulate in the bleb and diffuse through the conjunctiva to the tear film and tear ducts or through the sclera into the venous system of the eye. In this manner, aqueous humor is removed from the anterior chamber and into the bleb where it diffuses out and the intraocular pressure (IOP) in the anterior chamber is thereby reduced, thereby arresting glaucoma.

In order to facilitate placing the glaucoma drainage shunt in the eye, an inserter, described in FIG. 9 of the U.S. Pat. No. 7,431,709 was developed. This inserter 31, reproduced from the U.S. Pat. No. 7,431,709 here as FIGS. 3A and 3B, is comprised of a handle 32 and a slotted needle 33 that slidely fits within outer needle 34. Thumb slide 35 is rigidly attached to slotted needle 33. The glaucoma drainage shunt 1 is loaded in slotted tip 33 of the inserter 31, as shown in the enlarge tip in FIG. 3B. The tab 3 sticks out from a slot 36 in the slotted tip 33 of inserter 31.

A needle tract is first made in the eye in the area where the glaucoma drainage shunt 1 is to be placed. The slotted tip 33 of inserter 31, which contains the glaucoma drainage shunt 1, is inserted into the needle tract until tab 3 rests against the needle tract entrance; i.e., the sclera of the eye. The thumb slide 35, attached to slotted tube 33 is then pulled backwards relative to the glaucoma drainage shunt, which is held stationary by means of tab 3 resting against outer, stationary tube 34, and the slotted needle 33 is retracted, leaving the glaucoma drainage shunt 1 behind in the needle tract of the eye. FIG. 2 shows the glaucoma drainage shunt 1 in its final resting position in the eye. A needle tract is preferably made first as it can be difficult to insert the slotted tube 33 in the eye due to part of the cutting tip of the tube (needle) being removed to accommodate the slot, which accommodates the tab 3.

There are several problems associated with the inserter 31 of FIG. 3A used in conjunction with the glaucoma drainage shunt 1 of FIGS. 1 and 2. The inserter 31 is large and quite often the patient's nose or forehead is in the way and the inserter tip 33 cannot be maneuvered into the proper position to follow the needle tract. Bending the needle to allow a better approach prevents slotted tube 33 from sliding in outer tube 34; therefore the needle assembly cannot be bent. Also, the SIBS material of the glaucoma drainage shunt is soft and sticky (having a durometer of Shore 10A to 60A) and does not slide well in the slotted needle of the inserter and often jams, which delays the insertion procedure or can damage the shunt. Moreover, tissue can protrude into slot 33 of the inserter, binding the glaucoma drainage shunt and causing it to buckle when inserted in the needle tract. Further, the outer diameter of the inserter needle is large and stretches the needle tract. When the needle tip is in the needle tract, fluid can flow around the glaucoma drainage shunt and within the needle lumen and deflate the eye (i.e., a condition termed "hypotony"), which can lead to adverse events including retinal detachment, and the like. Also, tab 3 of the glaucoma drainage shunt 1 may at times rotate upward like the dorsal fin on a shark; when this occurs, the tab 3 can erode through the conjunctiva and cause infections.

The tab 3 of the glaucoma drainage shunt 1 was designed to work in tandem with slotted tube 33 of the inserter device 31. Over time, the design of the glaucoma drainage shunt was changed to shunt 41 as shown in FIG. 4 where the tab 43 is made symmetrical and atraumatic so as not to erode through the conjunctiva.

Also, the glaucoma drainage shunt 41 can be introduced into the needle tract with a forceps 50 into the eye as shown in FIG. 5. However, there are problems associated with using a forceps. For example, inserting the glaucoma drainage shunt 41 into the needle tract with the forceps 50 is difficult because as the glaucoma drainage shunt 41 is floppy and can buckle. The insertion of the glaucoma drainage shunt 41 is slow and unpredictable because the glaucoma drainage shunt 41 buckles when pushed from its proximal end and, thus, has to be incrementally pushed from the section of the tube near the entrance to the needle tract.

Another arrangement for inserting the drainage shunt 41 is shown in FIG. 6, which shows the glaucoma drainage shunt 41 of FIG. 4 in conjunction with a wire stylet 60 connected to handle 61. The stylet 60 passes through the lumen of the tube of the shunt 41. There are also numerous problems with using the arrangement shown in FIG. 6. Although the stylet 60 helps stiffen the tube, the stylet 60 is made from a very small diameter wire, in the order of 70 μm, which renders it inadvertently sharp and it often lodges in the fibrous tissue of the needle tract, preventing insertion of the glaucoma drainage shunt 41 into the needle tract. In addition, the soft tube of the shunt 41 is prone to collapsing, accordion-like, over the stylet 60, which prevents insertion of the shunt 41 into the needle tract. Lastly, the stylet 60 often adheres to the lumen of the shunt 41 and thus is difficult to remove from the shunt 41 without dislodging the shunt.

In yet another example, FIGS. 7A to 7D show an alternate approach where the glaucoma drainage shunt 41 of FIG. 5 is used in conjunction with an assembly 70 that includes a trocar 74 that extends over a needle 71. Specifically, the assembly 70 includes a hypodermic-type needle 72 extending from a hub 71. The needle 72 has a sharpened end 72 that is inserted into the eye 73. The trocar 74 is a thin-walled over-tube with a beveled distal end. A slot 75 is formed through the sidewall of the trocar 74 at its distal end and extends proximally in a direction parallel to the central axis of the tube 74. The trocar 74 can be made from metal or a hard plastic, such as polyimide. The needle shaft extends through the lumen of the over-tube 74 and is configured so that the sharp end 72 of the needle shaft extends beyond the beveled distal end of the over-tube 74 as shown in FIG. 7A. In this configuration, the sharp end 72 of the needle shaft is used to penetrate the eye and form a needle tract leading into the eye. The beveled distal end of the trocar 74 passes through the needle tract and enters the eye as the assembly (trocar and needle) are pushed into the eye, thereby enlarging the needle tract slightly. The needle 70 is then removed leaving the trocar 74 behind as shown in FIG. 7B. Glaucoma drainage shunt 41 is then inserted into slot 75 of trocar 74 with a forceps (not shown) as depicted in FIG. 7C. The trocar 74 is then removed leaving the glaucoma drainage shunt 41 behind and passing through the tract into the eye as shown in FIG. 7D.

There are problems associated with the approach of FIGS. 7A to 7D. First, it is difficult to push the needle 71 in place with the trocar 74 on the needle 71. Secondly, when the needle 70 is removed from the trocar 74 to leave behind the trocar 74 passing through the tract (FIG. 7B), aqueous humor leaks through the trocar 74, which can allow for unwanted deflation of the eye (i.e., a condition termed "hypotony"). Thirdly, when the trocar 74 is removed from the eye to leave behind the shunt 41 passing through the tract (FIG. 7D), the trocar can drag the glaucoma drainage shunt 41 out with it.

An alternate arrangement to that shown in FIGS. 7A to 7D (not shown) was attempted where the needle tract was made first with a sharp needle, then the glaucoma drainage shunt, which was preloaded with the glaucoma tube in a sharp metal trocar was inserted into the needle tract. The glaucoma drainage shunt was held with a forceps and the trocar removed. The problem with this alternate arrangement is that the glaucoma drainage shunt often came out with the trocar. In addition, aqueous humor leaked around the glaucoma drainage shunt and the eye deflated.

SUMMARY

An inserter for inserting a tubular medical implant device into tissue is described. The inserter includes a rigid rod extending along a longitudinal axis. The rod has a distal portion that defines an open slot. The open slot extends diametrically through the rod along the longitudinal axis to a base. The open slot is configured to receive the tubular medical implant device.

In one embodiment, the rod has a distal end, and the open slot is defined by two opposed fingers that extend from the base distally parallel to the longitudinal axis to distal ends of the fingers at the distal end of the rod.

In one embodiment, each finger has a planar inner surface that extends parallel with the longitudinal axis from a proximal end of the finger at the base to the distal end of the finger. The planar inner surfaces of the fingers are parallel to each other and the distal ends of the two opposed fingers define an opening that leads into the slot.

Also, in one embodiment, the base of the slot is defined by a diametrically extending circular bore extending along a first transverse axis orthogonal to the longitudinal axis of the rod where the first transverse axis and the transverse axis define a plane that extends parallel to a plane defined by the slot.

In yet another embodiment, the rod can be attached to a handle at a distal portion thereof. A proximal portion of the handle can be being offset from the longitudinal axis of the rod.

The features described in this summary and the following detailed description are not exhaustive. Additional features will be apparent to one of ordinary skill in the art in view of the drawings, specification, and claims hereof.

DETAILED DESCRIPTION

In accordance with the present application, an inserter device is provided for inserting a tubular medical implant device into the body. The inserter device is particularly suited for inserting the glaucoma drainage shunt 41 of FIG. 4, which is formed from a soft and flexible material, into the eye. The soft flexible material of the shunt 41 can lead to buckling of the shunt 41 in the event that shunt 41 is pushed from its distal end.

Figure 8A:
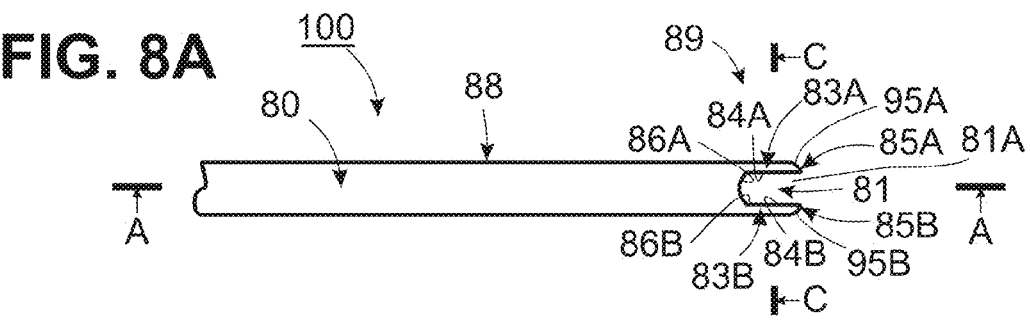
FIG. 8A is a schematic top view of a first embodiment of an inserter device according to the present application.
Figure 8B:
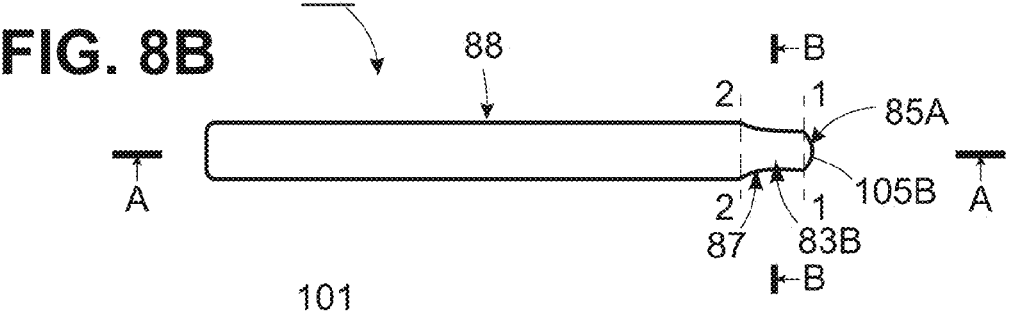
FIG. 8B is a schematic side view of the inserter device of FIG. 8A; the side view of FIG. 8B is 90 degrees orthogonal to the top view of FIG. 8A.

FIGS. 8A and 8B show the working end of an exemplary embodiment of an inserter 100, which includes a rigid rod 80

(preferably realized from metal) that is of a diameter preferably in the range between 0.012" to 0.025" (or 30 G to 22 G). The rod 80 includes a proximal portion 88 and a distal portion 89 adjacent to the proximal portion. A slot or bore 81 is formed in the distal portion 89 of the rod 80. The slot 81 extends diametrically through rod 80 in a direction of a first transverse axis B-B, that is transverse to longitudinal axis A-A of the rod 80, through a distal portion of the rod 80, and extends proximally in a direction parallel to axis A-A.

The slotted distal portion of the rod 80 defines two opposed fingers 83A, 83B (referred to in the culinary arts as a "fork") that extend parallel to one another in a direction parallel to the central axis A-A of the rod. The fingers 83A, 83B can have planar inner surfaces 84A and 84B. The fingers 83A, 83B extend from proximal ends 86A, 86B to distal ends 85A, 85B. The distal ends 85A, 85B of the two opposed fingers 83A, 83B define an opening 81A (FIG. 8A) that is part of the slot 81. The leading distal-most surfaces of the distal ends 85A, 85B can be rounded about the first transverse axis B-B, as shown in FIG. 8A, and about a second transverse axis C-C orthogonal to longitudinal axis A-A and first transverse axis B-B, as shown in FIG. 8B, in order to aid in insertion into a tissue tract leading into the eye. Lateral edges 87 of the sides of the two fingers 83A, 83B can also be tapered as best shown in FIG. 8B in order to aid in insertion into a tissue tract leading into the eye. Thus, measured along the second axis B-B, the fingers 83A and 83B have a smaller dimension at location 1 (proximate to the distal end of the fingers) in FIG. 8B than at location 2 (proximate to the proximal ends 86A, 86B in FIG. 8B. The slot 81 and opening 87 are both configured to receive and hold in place the soft tubular body of the medical implant device, such as the soft tube 42 of the glaucoma drainage shunt 41 of FIG. 4. For example, the distance between surfaces 84A and 84B of fingers 83A and 83B, as measured along the second transverse axis C-C is dimensioned to receive and hold in place the tubular body of the medical implant device.

Figure 9:
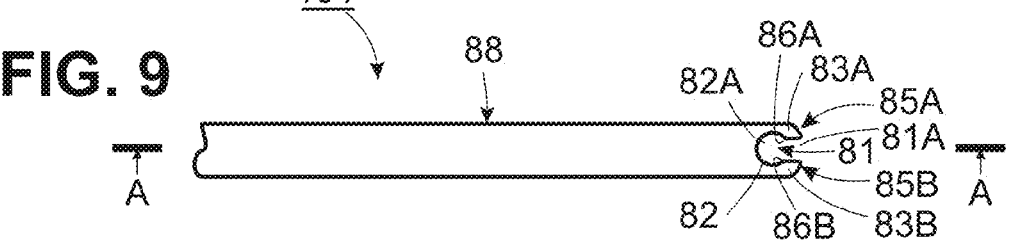
FIG. 9 is a schematic top view of a second embodiment of an inserter device according to the present application.
Figure 10:
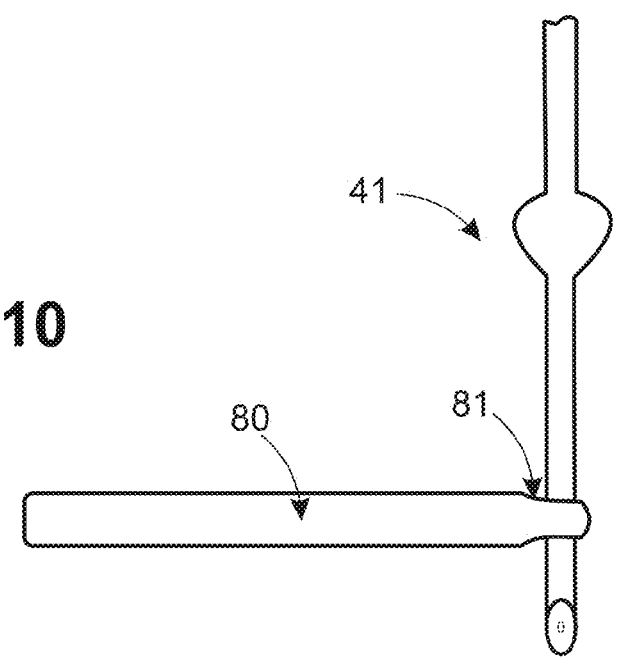
FIG. 10 is schematic view that shows the glaucoma drainage shunt of FIG. 4 captured by the opposed fingers disposed at the slotted distal end of the inserter of FIGS. 8A and 8B and FIG. 9.

FIG. 9 shows an alternative embodiment of an inserter 101, in which reference numbers refer to similar features of inserter 100, described above. In inserter 101, a slotted keyhole 82 can be formed in the distal portion 89 of the rod 80, as shown in FIG. 9. The slotted keyhole 82 is defined by a diametrically extending circular bore 82A and slot 81 extending distally from the circular bore. The keyhole 82 extends in a direction of a second axis B-B, transverse to longitudinal axis A-A of the rod 80, through a distal portion of the rod 80, and extends proximally in a direction parallel to longitudinal axis A-A. The slotted distal portion of the rod 80 defines two fingers 83A, 83B that are disposed opposite one another. The fingers 83A, 83B can have planar inner surfaces 84A and 84B. The fingers 83A, 83B extend from proximal ends 86A, 86B to distal ends 85A, 85B. The distal ends 85A, 85B of the two opposed fingers 83A, 83B define an opening 81A (FIG. 8A) that leads into the slot 81.

As shown in FIG. 8A, curved edges 95A, 95B are formed at the distal ends 85A, 85B of the fingers 83A, 83B about first transverse axis B-B. Also, leading distal-most edges 105A, 105B of the distal ends 85A, 85B can be rounded about second transverse axis C-C, that is orthogonal to longitudinal axis A-A and first transverse axis B-B, as shown in FIG. 8B. The curved edges 95A, 95B, 105A, and 105B aid in insertion into a tissue tract leading into the eye. Lateral edges 87 of the sides of the two fingers 83A, 83B can also be tapered as best shown in FIG. 8B in order to aid in insertion into a tissue tract leading into the eye.

Figure 1:
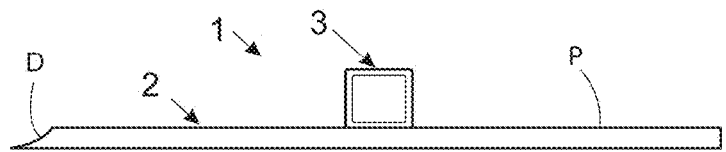
FIG. 1 is side view of a glaucoma drainage shunt described in U.S. Pat. No. 7,431,709.
Figure 2:
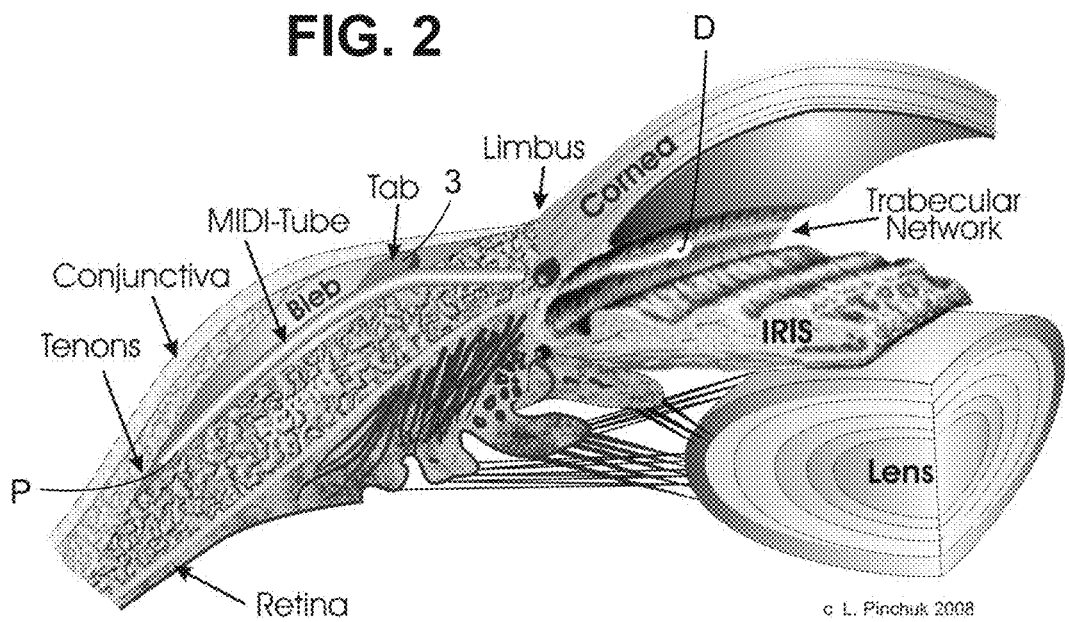
FIG. 2 is a schematic diagram that shows the glaucoma drainage shunt of FIG. 1 in its position implanted in the ocular environment.
Figure 3A:
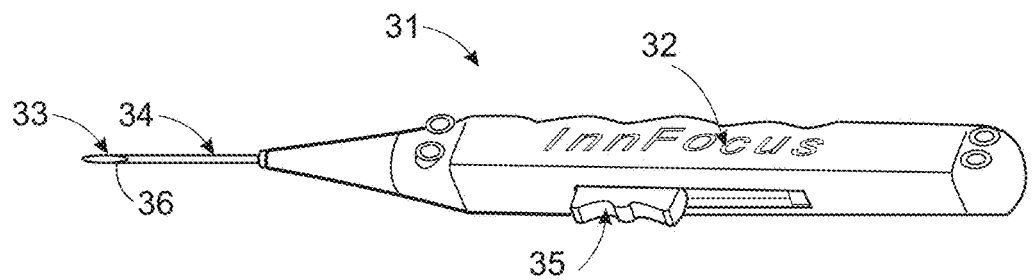
FIGS. 3A and 3B is a schematic diagram that illustrates an inserter device for use with the glaucoma drainage shunt of FIG. 1 as described in U.S. Pat. No. 7,431,709.
Figure 3B:
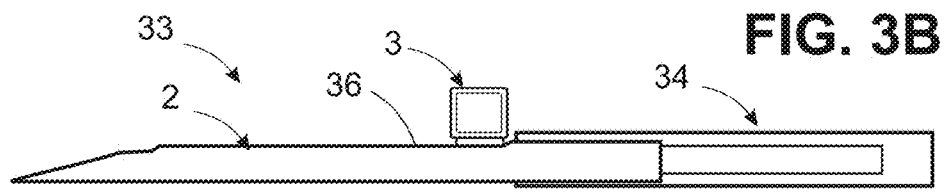
Figure 4:
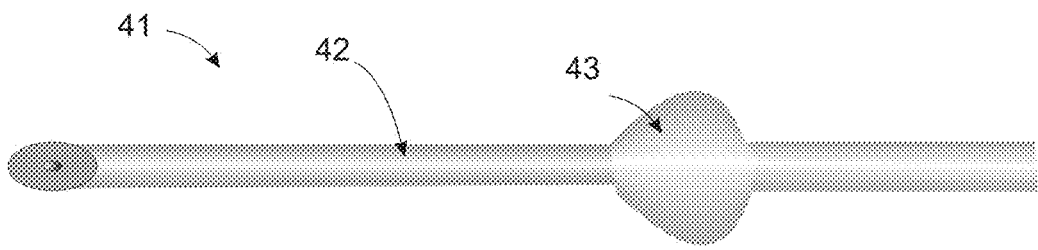
FIG. 4 is a top schematic view of a glaucoma drainage shunt with a symmetrical tab.
Figure 5:
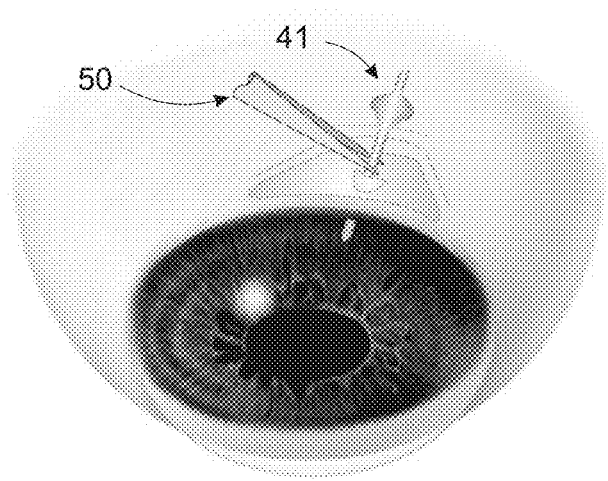
FIG. 5 is a schematic view showing the procedure for inserting the glaucoma drainage shunt of FIG. 4 with forceps.
Figure 6:
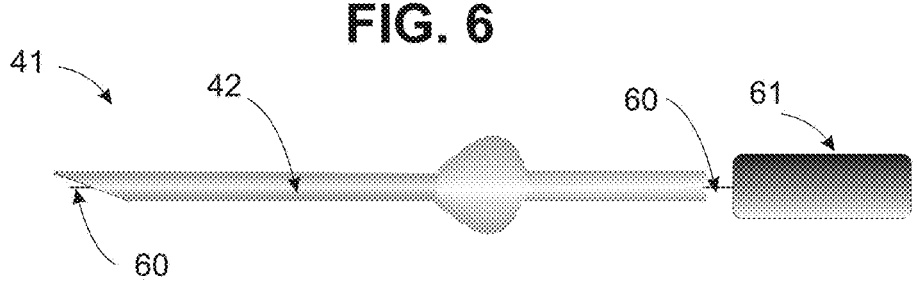
FIG. 6 is a schematic view of a wire stylet and handle that is used in conjunction with the glaucoma drainage shunt of FIG. 4.
Figure 7A:
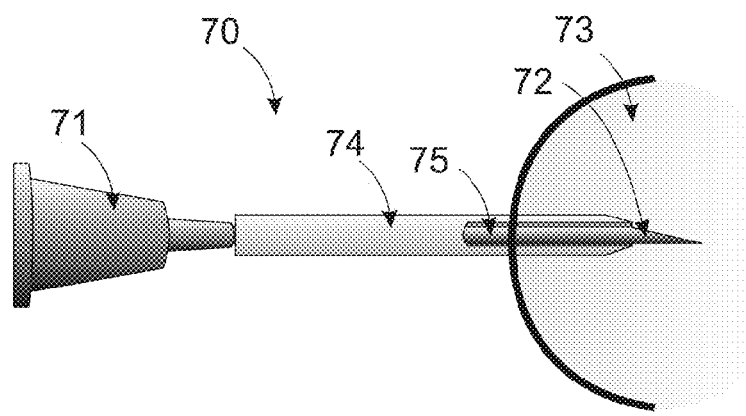
FIGS. 7A to 7D are schematic diagrams that illustrate the use of a trocar and needle assembly to insert the glaucoma drainage shunt of FIG. 4 into the eye.
Figure 7B:
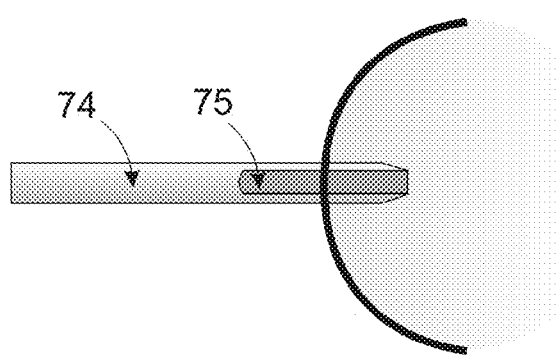
Figure 7C:
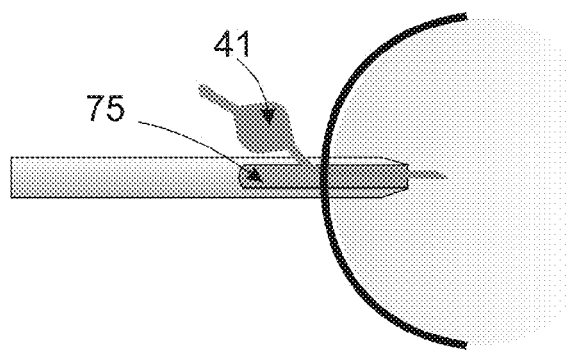
Figure 7D:
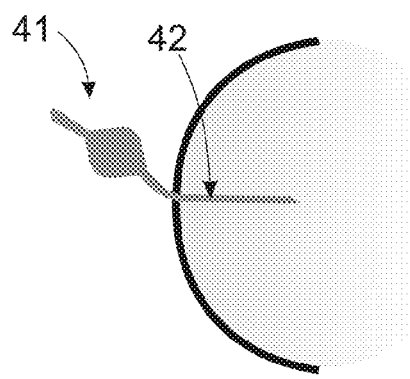

The keyhole 82 and the opening 81A leading into keyhole 82 are both configured to receive the soft tubular body 42 of the medical implant device 41, such as the soft tube 42 of the glaucoma drainage shunt 41 of FIG. 4. Such insertion can involve compression of the soft tubular body of the medical implant device. The opening 81A leading into the slotted keyhole 82 can be sized less than the outer radius of soft tubular body 42 in its relaxed uncompressed state in order to retain the soft tubular body 42 of the medical implant device 41 in the keyhole 82. This feature may be beneficial for packaging the device 41 on the inserter 101 as it will not take a set in this embodiment.

In an exemplary embodiment shown in FIGS. 10 and 11A to 11D, the tube 42 of the glaucoma drainage shunt 41 of FIG. 4 is held in slot 81 of inserter 100 (or circular bore 82A of keyhole 82 of inserter 101) of the rod 80 near the distal tip (1 mm to 3 mm from the distal end) of the tube 42 by means of the outer diameter of tube 42 (in its relaxed uncompressed state) being slightly larger than the maximal distance measured along second transverse axis C-C that separates the fingers of the slot 81 of inserter 100 (or diameter of the circular bore 82A of keyhole 82 of inserter 101) of the rod 80. In one embodiment, this maximal distance is 5% to 30% less than the outer diameter of tube 42 (in its relaxed uncompressed state) to enable holding and even packaging (i.e., pre-loading) the glaucoma drainage shunt 41 with the rod 80.

Figure 11A:
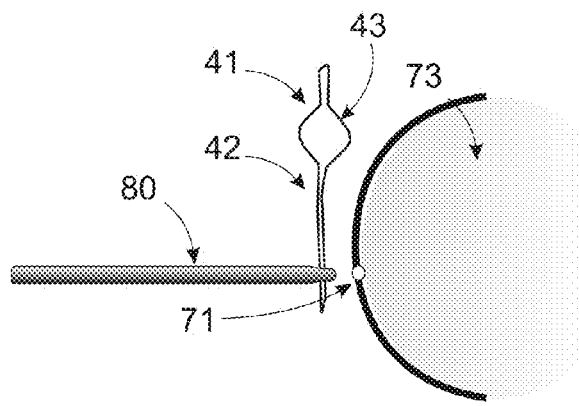
FIGS. 11A to 11D are schematic diagrams that illustrate the use of inserters of FIGS. 8A and 8B to insert the glaucoma drainage shunt of FIG. 4 into the eye.
Figure 11B:
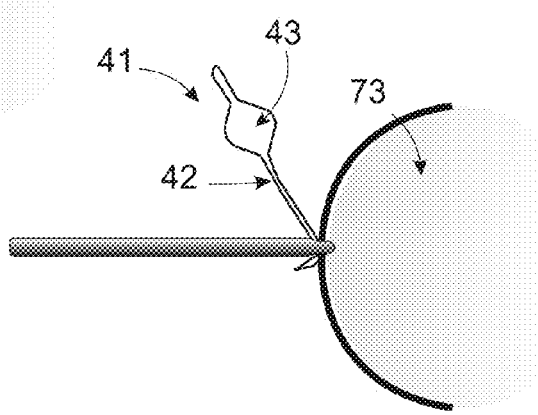
Figure 11C:
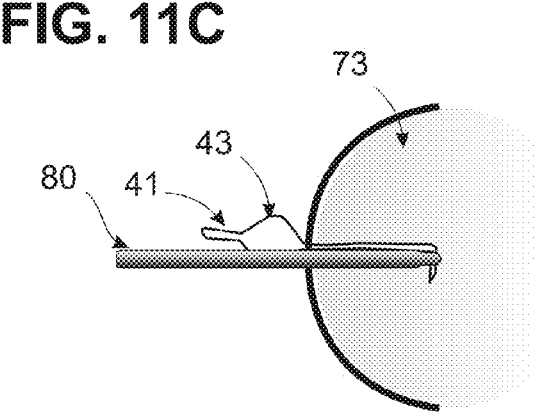
Figure 11D:
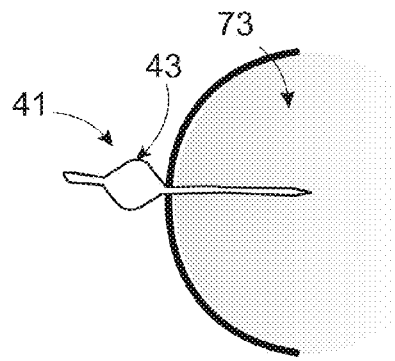

The following describes a shunt insertion procedure employing the inserters described above. During use, a needle tract 71 is formed that leads into the eye 73 as shown schematically in FIG. 11A. The needle tract can be made with a bent 25 G (0.02" diameter) needle that is stoppered to prevent aqueous from exiting the eye through the needle (the needle itself need not be hollow). If need be, the distal portion of the soft tube 42 of the glaucoma drainage shunt 41 is captured between the opposed fingers of the slot 81 of inserter 100 (or the circular bore 82A of keyhole 82 of inserter 101) of the rod 80 as shown in FIG. 11A. In this configuration, the rod 80 is manipulated so that the distal end of the rod 80 passes into and through the needle tract 71. The tube 42 of the glaucoma drainage shunt 71, being of a soft stretchable rubbery material conforms to the rod 80 as it passes through the needle tract 71 as shown in FIGS. 11B and 11C. Once the glaucoma drainage shunt 41 is fully in place, which is at the point where the fin 43 meets the sclera of the eye (FIG. 11C), the rod 80 is simply retracted backwards causing the soft tube 42 of the drainage shunt 41 to be released from its position between the opposed fingers of the slot 81 of inserter 100 (or the circular bore 82A of keyhole 82 of inserter 101) of the rod 80 and thus remains in place in the eye. In this position, the soft tube 42 of the drainage shunt 41 passes through the needle tract with the distal end (entrance) remaining inside the eye.

Figure 12:
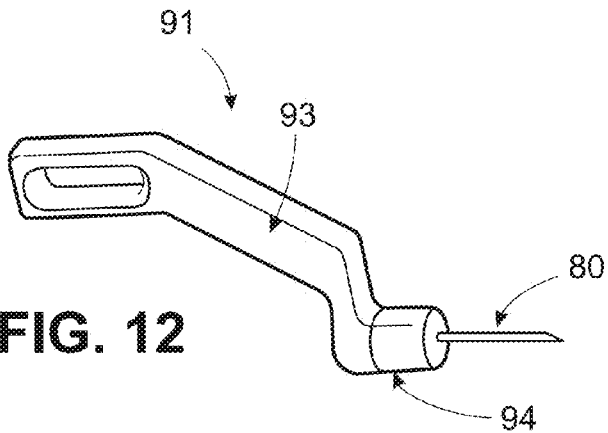
FIG. 12 is an isometric view of yet another exemplary embodiment of an inserter device according to the present application, which includes a handle that is mechanically coupled to the device of FIGS. 8A and 8B.

A handle 91 can be mechanically coupled to the proximal end of the rod 80 as shown in FIG. 12. The handle 91 can be formed from a plastic material such as polypropylene, polyethylene, ABS, polycarbonate, polyurethane, nylon, etc.). The handle 91 can have an extension arm 93 that is shaped to avoid interference with the patient's forehead and nose during the shunt insertion procedure. The rod 80 can be insert molded, press fit or otherwise attached to the handle 91. The area where the rod 80 attaches to the handle 91 can be rounded and tapered so as to enable placing a cap over the rod 80 to protect it during shipping. Rings or tubes (not shown) can be placed over the rod 80 to control the depth of penetration of the rod 80 into the eye. Alternatively, the length of rod 80 protruding from the handle can be controlled by a mechanical mechanism. The entire assembly of the handle 91 and the rod 80 can be disposable.

The inserters and methods described herein have advantages when used to insert the glaucoma drainage shunt of FIG. 4. As but one example, aqueous humor does not leak through the collapsed needle tract that is left behind when the needle is removed, thus reducing the risk of deflation of the eye. In addition, the glaucoma drainage shunt is releasably captured between the fingers of the distal working end of the inserter and can be packaged and sterilized in this manner. Also, the glaucoma drainage shunt, releasably captured between the fingers of the distal working end of the inserter, can be inserted into the needle tract without aqueous leaking around the inserter. The inserter has no moving parts and, thus, avoids any mechanism that can jam. The inserter can be used with a handle that minimizes interference from the forehead or nose of the patient. The glaucoma drainage shunt is introduced into the hole, which avoids buckling of the glaucoma drainage shunt and allows for quick and smooth insertion.

One well versed in the art would appreciate that the fingers can be milled and/or drilled into the rod. Alternatively the fingers can be comprised of wires that extend from a tube. The wires can be fixed into the tube by means of brazing, soldering or the use of an adhesive. One can also envision that a thin tube can be placed over the rigid rod with the fingers extending distally from the rod and thin tube. In said configuration, when a glaucoma device is held in the fingers, and the rigid rod retracted, with the thin tube held stationary, the glaucoma tube is released from the rigid rod by interference from the thin tube.

In another embodiment, the rigid rod can be configured with a mechanism wherein the fingers are actively closed by a collet-like action. Such collet-like actions are well-known in the art.

There have been described and illustrated herein several embodiments of a device for inserting a soft tubular medical implant device into the body. The inserter device is particularly suited for inserting the soft glaucoma drainage shunt 41 of FIG. 4 into the eye. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as claimed

What is claimed is:

1. An inserter system for inserting a tubular ocular shunt into an eye, the system comprising:
   a tubular ocular shunt having an elongated, compressible body defining a central lumen; and
   an elongated rigid rod extending along a longitudinal axis, the rod having a distal portion that defines an open slot, wherein the open slot extends through the rod along the longitudinal axis from an open end to a base, and extends diametrically through the rod along a first transverse axis that is transverse to the longitudinal axis, wherein the open slot is dimensioned to receive and retain a portion of the tubular ocular shunt in a compressed state and with the lumen of the retained portion of the shunt being aligned with the first transverse axis and extending diametrically completely across the slot and through the rod, and wherein a distal end of the rod is configured for insertion through a tissue passageway leading into the eye together with the portion of the tubular ocular shunt that is received and retained in the compressed state by the open slot of the rod.

2. The inserter system according to claim 1, wherein: the open slot is defined by two opposed fingers that extend from the base distally parallel to the longitudinal axis to distal ends of the fingers at the distal end of the rod.

3. The inserter system according to claim 2, wherein each finger has a planar inner surface that extends parallel with the longitudinal axis from a proximal end of the finger at the base to the distal end of the finger, and wherein the planar inner surfaces of the fingers are parallel to each other, and wherein the distal ends of the two opposed fingers define an opening that leads into the slot.

4. The inserter system according to claim 3, wherein each finger has a curved outer surface opposite the planar inner surface.

5. The inserter system according to claim 4, wherein for each finger, the distal end of the finger is defined by a curved edge between the inner planar surface and the curved outer surface.

6. The inserter system according to claim 5, wherein the curved edge is curved about the first transverse axis, wherein the first transverse axis and the longitudinal axis define a plane that extends parallel to the plane of the inner surface.

7. The inserter system according to claim 6, wherein each finger is curved at its distal end about a second transverse axis that is transverse to the longitudinal axis and the first transverse axis.

8. The inserter system according to claim 7, wherein the width of the finger, measured along the first transverse axis, is less at the distal end of the finger than at the proximal end of the finger.

9. The inserter system according to claim 8, wherein the slot is constructed to receive the portion of the tubular ocular shunt oriented longitudinally along the first transverse axis.

10. The inserter system according to claim 2, wherein the base of the slot is defined by a diametrically extending circular bore extending along the first transverse axis where the first transverse axis and the transverse axis define a plane that extends parallel to a plane defined by the slot.

11. The inserter system according to claim 10, wherein the diameter of the circular bore is larger than the distance between opposed, planar inner surfaces of the fingers.

12. The inserter system according to claim 11, wherein the distance between the planar inner surfaces of the fingers is less than the outer diameter of a tubular body of the ocular shunt when the shunt is in a relaxed state.

13. The inserter system according to claim 10, wherein each finger has a curved outer surface opposite the planar inner surfaces of the fingers.

14. The inserter system according to claim 13, wherein for each finger, the distal end of the finger is defined by a curved edge between the inner planar surface and the curved outer surface.

15. The inserter system according to claim 14, wherein the curved edge is curved about the first transverse axis.

16. The inserter system according to claim 15, wherein each finger is curved at its distal end about a second transverse axis orthogonal to both the longitudinal axis and the first transverse axis.

17. The inserter system according to claim 16, wherein the width of the finger, measured along the first transverse axis, is less at the distal end of the finger than at its proximal end.

18. The inserter system according to claim 17, wherein the slot is constructed to receive the portion of the tubular ocular shunt oriented longitudinally along the first transverse axis.

19. The inserter system according to claim 1, further comprising a handle having a distal portion and a proximal portion, the distal portion of the handle attached to the rod, the proximal portion of the handle being offset from the longitudinal axis of the rod.

20. The inserter system according to claim 1, wherein the rigid rod has a diameter of up to 0.025 inch, and wherein the open slot is dimensioned smaller than the diameter of the rigid rod.

21. The inserter system according to claim 1, wherein a maximum dimension of the open slot is 5% to 30% less than the outer diameter of the portion of the tubular ocular shunt in its relaxed, uncompressed state.

22. The inserter system according to claim 1, wherein the open slot is dimensioned to receive and retain a distal portion of the tubular ocular shunt.

23. A method of inserting a tubular ocular shunt into an eye, the tubular ocular shunt having an elongated, compressible body defining a central lumen, the method comprising:
provide an inserter for inserting the tubular ocular shunt into the eye, the inserter comprising:
an elongated rigid rod extending along a longitudinal axis, the rod having a distal portion that defines an open slot, wherein the open slot extends through the rod along the longitudinal axis from an open end to a base, and extends diametrically through the rod along a first transverse axis that is transverse to the longitudinal axis, wherein the open slot is dimensioned to receive and retain a portion of the tubular ocular shunt in a compressed state and with the lumen of the retained portion of the shunt being aligned with the first transverse axis and extending diametrically completely across the slot and through the rod, and wherein a distal end of the rod is configured for insertion through a tissue passageway leading into the eye together with the portion of the tubular ocular shunt that is received and retained in the compressed state by the open slot of the rod;
disposing the portion of the tubular ocular shunt in the slot, wherein the disposed portion is retained in the slot in a compressed state; and
inserting the distal portion of the rod and the tubular ocular shunt in a first direction into the tissue passageway.

24. The method according to claim 23, further comprising moving the rod in a second direction different from the first direction to remove the tube from the slot to deposit the tubular implant device in the tissue.

25. The method according to claim 24, wherein the second direction is opposite the first direction.

26. The method according to claim 23, further comprising removing the rod from the tissue to remove the tube from the slot to deposit the tubular implant device in the tissue.

27. The method according to claim 23, wherein a distal portion of the tubular implant device is introduced into the slot.

28. The method according to claim 23, wherein the rod and tubular implant device are inserted through a tract formed in the tissue.

29. A method of inserting a tubular ocular shunt into an eye, the tubular ocular shunt having an elongated, compressible body defining a central lumen, the method comprising:
providing an inserter for inserting the tubular medical implant device into tissue, the inserter comprising:
an elongated rigid rod extending along a longitudinal axis, the rod having a distal portion that defines an open slot, wherein the open slot extends through the rod along the longitudinal axis from an open end to a base, and extends diametrically through the rod along a first transverse axis that is transverse to the longitudinal axis, wherein the open slot is dimensioned to receive and retain a portion of the tubular ocular shunt in a compressed state and with the lumen of the retained portion of the shunt being aligned with the first transverse axis and extending diametrically completely across the slot and through the rod, and wherein a distal end of the rod is configured for insertion through a tissue passageway leading into the eye together with the portion of the tubular ocular shunt that is received and retained in the compressed state by the open slot of the rod, wherein the tubular implant device is disposed in the slot in the compressed state; and
inserting the distal portion of the rod and the tubular ocular shunt in a first direction into the tissue passageway.

30. The method according to claim 29, further comprising moving the rod in a second direction different from the first direction to remove the tube from the slot to deposit the tubular implant device in the tissue.

31. The method according to claim 29, wherein the rod and tubular implant device are inserted through a tract formed in the tissue.

* * * * *